United States Patent [19]

Rogers et al.

[11] 4,215,127
[45] Jul. 29, 1980

[54] SUBSTITUTED 1-PHENOXY-1-TRIAZOLYL-2-BUTANONE COMPOUNDS AND THEIR USE AS FUNGICIDES

[75] Inventors: Richard B. Rogers, Concord; Chrislyn M. Carson; Robert J. Ehr, both of Pittsburg, all of Calif.

[73] Assignee: The Dow Chemical Company, Midland, Mich.

[21] Appl. No.: 956,956

[22] Filed: Nov. 2, 1978

[51] Int. Cl.² .................... A01N 9/22; C07D 249/08
[52] U.S. Cl. .................. 424/269; 106/18.32; 106/18.33; 252/51.5 R; 252/106; 260/45.8 NT; 548/262
[58] Field of Search .................. 260/308 R; 424/269

[56] References Cited

U.S. PATENT DOCUMENTS

| | | | |
|---|---|---|---|
| 3,897,438 | 7/1975 | Drabes et al. | 260/308 A |
| 4,038,318 | 9/1977 | Meiser et al. | 424/269 |
| 4,154,842 | 5/1979 | Krämer et al. | 424/269 |

FOREIGN PATENT DOCUMENTS

| | | | |
|---|---|---|---|
| 2201063 | 7/1973 | Fed. Rep. of Germany | 260/308 R |
| 2247186 | 3/1974 | Fed. Rep. of Germany | 260/308 R |

*Primary Examiner*—Alton D. Rollins
*Attorney, Agent, or Firm*—S. Preston Jones

[57] ABSTRACT

Substituted 1-phenoxy-1-triazolyl-2-butanone compounds which correspond to the formula

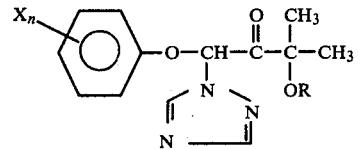

wherein each X independently represents chloro, bromo, iodo, nitro, methyl, methoxy, or methylthio; n represents an integer of 0 to 3; and R represents methyl or ethyl. These compounds have been found to exhibit a high degree of fungicidal activity, and compositions containing said compounds are so employed.

24 Claims, No Drawings

SUBSTITUTED 1-PHENOXY-1-TRIAZOLYL-2-BUTANONE COMPOUNDS AND THEIR USE AS FUNGICIDES

DESCRIPTION OF PRIOR ART

1-Phenoxy-1-(1,2,4-triazolyl)-2-alkanone compounds and derivatives having fungicidal activity are disclosed in German Offen. 2,201,063 (Chemical Abstracts 79, 105257y (1973)) and German Offen. 2,247,186 (Chemical Abstracts 80, 146169k (1974)).

SUMMARY OF THE INVENTION

The present invention is directed to novel substituted 1-phenoxy-1-triazolyl-2-butanone compounds, to compositions containing said active compounds, and to the use of such compositions for controlling fungi that attack plants. The compounds of the present invention correspond to the formula

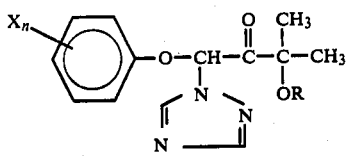

wherein each X independently represents chloro, bromo, iodo, nitro, methyl, methoxy, or methylthio; n represents an integer of 0 to 3; and R represents methyl or ethyl.

The compounds of the invention are solids or oily liquids at ambient temperatures and are of low mammalian toxicity. The compounds are substantially insoluble in water and usually are moderately to highly soluble in common organic solvents.

The compounds of the present invention can be prepared by the reaction of substantially equimolar amounts of 1H-1,2,4-triazole with an appropriate 1-halo-1-phenoxy-2-butanone compound corresponding to the formula

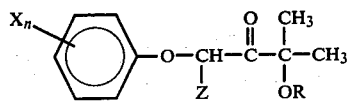

wherein X, n, and R are as defined hereinabove, and Z is bromo or chloro. The reaction is carried out in presence of a solvent and a hydrogen halide acceptor. Preferably the reaction is carried out at a temperature within the range of from $-10°$ to $110°$ C., most preferably from $0°$ to $35°$ C.

Alternatively, the compounds of the present invention can be prepared by the reaction of substantially equimolar amounts of 1H-1,2,4-triazole, a phenol of the formula

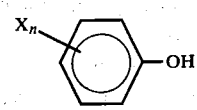

and a 1,1-dihalo-2-butanone compound of the formula

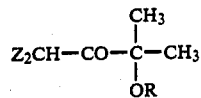

wherein X, n, R, and Z are as defined hereinabove. The reaction is carried out in presence of a solvent and a hydrogen halide acceptor. The reaction can be carried out at a temperature within the range of from $0°$ C. to reflux temperature, i.e., the boiling temperature of the reaction mixture.

Suitable solvents useful in carrying out the reactions include acetone, acetonitrile, halogenated hydrocarbon solvents such as methylene chloride, and hydrocarbon solvents such as hexane, benzene, or toluene. Suitable hydrogen halide acceptors useful in carrying out the reaction include conventional bases, such as potassium or sodium carbonate, triethylamine and 1,5-diaza(5,4,0)undec-5-ene as is well known to those skilled in the art.

The products of the reactions can be purified as desired using appropriate well known procedures, such as recrystallization from a solvent or distillation.

DESCRIPTION OF SOME PREFERRED EMBODIMENTS

The following examples illustrate the present invention and the manner by which it can be practiced, but as such, should not be construed as limitations on the overall scope of the same.

EXAMPLE I

1-Bromo-1-(2,4-dichlorophenoxy)-3-methoxy-3-methyl-2-butanone (Intermediate)

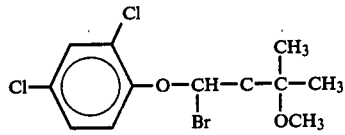

To a stirred mixture of 66 grams (g) powdered 85% potassium hydroxide (1 mole) and 500 ml. diglyme was added 84.1 g (1.0 mole) 2-methyl-3-butyn-2-ol. An exotherm was observed. The mixture was cooled in a cold water bath at about $15°$ C., and 142 g (1.0 mole) methyliodide at a rate to maintain the temperature of the reaction mixture at $20°$–$25°$ C. After the addition was complete, the cooling bath was removed and stirring continued at room temperature. The temperature of the mixture slowly rose to $40°$, then returned to room temperature. After stirring overnight, the mixture was distilled and all material boiling up to $100°$ collected. Pentane (100 ml.) was added to the distillate and the organic phase separated, dried using $MgSO_4$, and purified by distillation to give 64.8 g (67% yield) of 3-methoxy-3-methyl-1-butyne, b.p. $80°$–$82°$ C.

A mixture of 90.0 g (0.926 mole) of 3-methoxy-3-methyl-1-butyne, 38 g (2.1 mole) of water, 70 ml of methanol, 12.55 g (0.042 mole) of mercuric sulfate, and 0.6 ml of concentrated sulfuric acid was heated at reflux temperature with stirring for 3.5 hours. The mixture slowly became homogenous, then a solid separated. The solid was filtered, washed with methanol, and the filtrate was poured into one liter of a saturated aqueous NaCl solution. The organic phase was separated and the aqueous phase was extracted with methylene chloride. The organic phases were combined, dried using MgSO4, and distilled to give 75.2 g (70% yield) of 3-methoxy-3-methyl-2-butanone, b.p. 122° C.

Bromine (26.42 g, 0.165 mole) was slowly added to a stirred solution of 19.2 g (0.165 mole) of 3-methoxy-3-methyl-2-butanone in 400 ml. diethyl ether at 15° C. After the addition was complete, the solvent was evaporated, and the residual orange oil distilled to give 22 g (68% yield) of 1-bromo-3-methoxy-3-methyl-2-butanone, b.p. 57°-59° C./1.7 mm. Hg.

A stirred mixture of 13.04 g (0.08 mole) of 2,4-dichlorophenol, 15.61 g (0.08 mole) 1-bromo-3-methoxy-3-methyl-2-butanone, and 11.1 g (0.08 mole) powdered potassium carbonate in 300 ml acetonitrile was heated at reflux temperature for 30 minutes. The reaction mixture was cooled, filtered, and the solvent evaporated from the filtrate. The residual oil was taken up in hexane and cooled to −20° C., whereupon the product separated as a white crystalline solid. There was thus obtained 19 g (85.7% yield) of 1-(2,4-dichlorophenoxy)-3-methoxy-3-methyl-2-butanone, m.p. 45.5°-47.5° C.

Bromine (10.73 g, 0.067 mole) was slowly added to a stirred solution of 18.6 g (0.067 mole) of 1-(2,4-dichlorophenoxy)-3-methoxy-3-methyl-2-butanone in 350 ml diethyl ether containing 0.2 g aluminum chloride at about 3° C. After the addition, the mixture was stirred an additional 30 minutes, then poured into aqueous sodium bisulfite. The organic layer was separated, extracted with sodium bicarbonate solution, dried using MgSO4, and the solvent evaporated. There was thus obtained 23.6 g (99% yield) of 1-bromo-1-(2,4-dichlorophenoxy)-3-methoxy-3-methyl-2-butanone.

EXAMPLE II 1-(2,4-Dichlorophenoxy)-1-(1H-1,2,4-triazol-1-yl)-3-methoxy-3-methyl-2-butanone

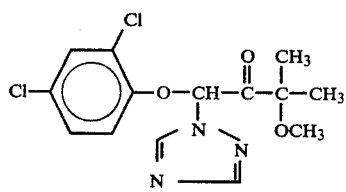

1H-1,2,4-Triazole (2.83 g, 0.041 mole) was added to a stirred solution of 14.6 g (0.041 mole) of 1-bromo-1-(2,4-dichlorophenoxy)-3-methoxy-3-methyl-2-butanone in 100 ml. of acetone at −10° C. To the resulting mixture, 6.09 g (0.041 mole) of 1,5-diazabicyclo[5.4.0]-undec-5-ene was added at a rate to maintain the temperature of the mixture below −5° C. After the addition was complete, the mixture was stirred an additional 30 minutes at 0° C. Then the solvent was evaporated off, the residue taken up in 300 ml. diethyl ether, and the resulting mixture extracted with water. The organic phase was dried using MgSO4 and the solvent evaporated. The residual yellow oil (13 g) was stirred for several minutes with boiling hexane, then filtered to remove insoluble material. Upon cooling the filtrate, 9.0 g (63.8% yield) of 1-(2,4-dichlorophenoxy)-1-(1H-1,2,4-triazol-1-yl)-3-methoxy-3-methyl-2-butanone, m.p. 53°-54° C., was obtained.

| Elemental analysis: | | | |
|---|---|---|---|
| | C | H | N |
| Theory for C14H15Cl2N3O3 | 48.85 | 4.39 | 12.21 |
| Found | 48.82 | 3.91 | 12.25 |

EXAMPLE III 1-(4-Iodophenoxy)-1-(1H-1,2,4-triazol-1-yl)-3-methoxy-3-methyl-2-butanone

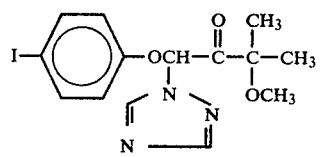

A mixture of 9.9 g (0.045 mole) of 4-iodophenol, 3.45 g (0.05 mole) of 1H-1,2,4-triazole, 12.33 g (0.045 mole) of 1,1-dibromo-3-methoxy-3-methyl-2-butanone, and 14 g (0.101 mole) of potassium carbonate in 200 ml of acetone was heated at boiling temperature (reflux) with stirring for 4 hours. After evaporating the solvent, 400 ml of 5% NaOH solution was added and the mixture extracted with diethyl ether. The ether phase was dried using MgSO4 and the solvent evaporated. The residual yellow oil was purified by high pressure liquid chromatography (silica gel, 8:2 hexane/acetone). Recrystallization from hexane-ether gave 8.0 g (44% yield) of 1-(4-iodophenoxy)-1-(1H-1,2,4-triazol-1-yl)-3-methoxy-3-methyl-2-butanone, m.p. 81.5°-82.5° C.

| Elemental Analysis: | | | |
|---|---|---|---|
| | C | H | N |
| Theory for C14H16IN3O3 | 41.91 | 4.02 | 10.47 |
| Found | 42.02 | 4.07 | 10.41 |

To a stirred solution of 23.23 g (0.2 mole) of 3-methoxy-3-methyl-2-butanone in 200 ml of ether was added dropwise 79.91 g (0.5 mole) of bromine. After the bromine color had disappeared, the mixture was poured into cold aqueous sodium bisulfite. The organic phase was separated, and the aqueous phase extracted with 200 ml of ether. The combined organic phases were dried and the solvent removed by evaporation leaving a yellow oil. NMR and gas chromatographic analysis indicated this material to be 1,1-dibromo-3-methoxy-3-methyl-2-butanone of greater than 95% purity.

Using procedures similar to Examples II and III, additional compounds of the present invention listed in Table I were prepared.

TABLE I

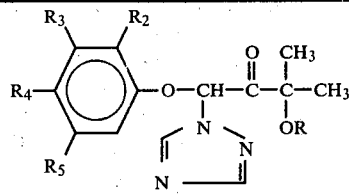

| Example No. | R | $R_2$ | $R_3$ | $R_4$ | $R_5$ | Melting Point °C. | | Elemental Analysis C | H | N |
|---|---|---|---|---|---|---|---|---|---|---|
| IV | $CH_3$ | H | H | Cl | H | 74.5–76.5 | T* | 57.24 | 5.49 | 14.30 |
| | | | | | | | F | 57.33 | 5.63 | 14.11 |
| V | $CH_3$ | Cl | H | Cl | Cl | 83–87.5 | T | 44.41 | 3.73 | 11.10 |
| | | | | | | | F | 44.36 | 3.11 | 10.96 |
| VI | $CH_3$ | H | Cl | H | Cl | 120–124 | T | 48.85 | 4.39 | 12.21 |
| | | | | | | | F | 48.64 | 4.07 | 11.70 |
| VII | $CH_3$ | H | Cl | Cl | H | $n_D^{25}$ 1.5413 | T | 48.85 | 4.39 | 12.21 |
| | | | | | | | F | 48.53 | 3.63 | 11.44 |
| VIII | $CH_3$ | H | H | $NO_2$ | H | 129–131 | T | 52.49 | 5.04 | 17.49 |
| | | | | | | | F | 52.31 | 4.90 | 17.55 |
| IX | $CH_3$ | H | H | H | H | 46–51 | T | 61.08 | 6.23 | 15.26 |
| | | | | | | | F | 60.53 | 5.96 | 15.14 |
| X | $C_2H_5$ | Cl | H | Cl | H | 93–95 | T | 50.29 | 4.78 | 11.73 |
| | | | | | | | F | 50.34 | 4.85 | 11.60 |
| XI | $CH_3$ | Br | H | Br | H | 80–81.5 | T | 38.82 | 3.49 | 9.70 |
| | | | | | | | F | 38.75 | 3.45 | 9.73 |
| XII | $CH_3$ | H | H | $CH_3$ | H | 58–59.5 | T | 62.27 | 6.62 | 14.52 |
| | | | | | | | F | 62.23 | 6.55 | 14.54 |
| XIII | $CH_3$ | H | H | $-SCH_3$ | H | 58–61 | T | 56.05 | 5.96 | 13.07 |
| | | | | | | | F | 56.11 | 6.03 | 13.04 |
| XIV | $CH_3$ | H | H | $-OCH_3$ | H | 45–47.5 | T | 59.02 | 6.24 | 13.69 |
| | | | | | | | F | 59.00 | 6.27 | 13.76 |

*T = Theory
F = Found

In accordance with this invention, it has been found that the compounds of the present invention are adapted to be employed as fungicidal agents for the control of a wide variety of fungal organisms. The compounds are particularly adapted to be employed for the control of fungal organisms found on plants, such as, for example, barley powdery mildew (*Erysiphe graminis hordeii*), grape downy mildew (*Plasmopara viticola*), wheat rusts (*Puccinia sp.*) verticillium wilt (*Verticillium albo-atrum*), apple powdery mildew (*Podosphaera leucotricha*), tobacco black root rot (*Thielaviopsis basicola*) or apple scab (*Venturia inaequalis*). In such uses, the compounds are usually applied to the aerial portions of plants. The compounds can also be applied in dormant applications to the woody surfaces of plants or to orchard floor surfaces for the control of overwintering spores of many fungi. In addition, the compounds can be applied to seeds to protect the foliage of growing plants from attack of fungal organisms such as those causing rust or mildew. Furthermore, the compounds can be applied or distributed in soil for control of fungal organisms that attack seeds or plant roots, particularly those organisms that cause root rot or wilt.

In further operations, the compounds can be included in inks, adhesives, soaps, cutting oils, polymeric materials, oil paints, or latex paints to prevent mold, mildew, or degradation of such materials resulting from microbial attack. Additionally, the compounds can be distributed in textile or cellulosic materials, or they can be employed in the impregnation of wood or lumber to protect such products from fungal organism which cause rot, mold, mildew, or decay.

It is an advantage of the present invention that compositions containing the compounds can be applied to vegetation or soil in amounts required for effective control without significant injury to plants. A further advantage is that the compounds exhibit very low mammalian toxicity at the rates employed for control of fungal organisms. Another advantage is that a single application of the compounds can provide a residual, extended control of fungi for a period of several months. Also, the compounds can be effective in eliminating established fungal infestation. Furthermore, the compounds have been found to be translocated in plants and thus can provide a systemic protection against fungi that attack plants.

Generally in the actual practice of the method of the present invention, a plant protecting amount of the toxicant compounds can be applied to the plant by such convenient procedures as soil injection, drenching with an aqueous composition, seed treatment, topical spraying, furrow spraying, or other techniques known to those skilled in the art.

The exact dosage of the active toxicant employed can be varied depending upon the specific plant, hardiness of the plant, and the mode of application. Generally, the active ingredient should be present in an amount equivalent to from about 50 micrograms to about 125 milligrams or more per plant. Translating this into conventional application rates, this amount is equivalent to from about 0.001 pound to about 2 pounds or more of the active ingredient on a per acre basis (0.0013–2.24 kilogram per hectare), as chemical available to the plant.

Larger amounts of the active ingredient advantageously may be applied when treatments are employed which distribute the material throughout the soil. For example, when the active ingredient is applied as an at-plant row treatment or as an early season post-plant side dress treatment, those amounts of chemical not proximal to plant roots are essentially unavailable to the plant and therefore not effective as set forth hereinabove. In such practices, amounts of the active ingredient need to be increased to rates as high as about 10 pounds per acre (11.2 kg/hectare) to assure the requisite effective quantity of active ingredient is made available to the plants.

The present invention can be carried out by employing the compounds directly, either singly or in combination. However, the present invention also embraces the employment of liquids, dusts, wettable powders, granules, or encapsulated compositions containing at least one of said compounds as active ingredient. In such usage, the compound or compounds can be modified with one or more of a plurality of additaments or adjuvants including inert solvents, inert liquid carriers, wetting agents, and/or surface active dispersing agents and coarsely or finely divided inert solids. The augmented compositions are also adapted to be employed as concentrates and subsequently diluted with additional inert carrier to produce other compositions in the form of dusts, sprays, granules, washes, or drenches. In compositions where the adjuvant is a coarsely or finely divided solid, a surface active agent, or the combination of a surface active agent and a liquid additament, the adjuvant cooperates with the active component so as to facilitate the invention. Whether the composition is employed in liquid, wettable powder, dust, granule, or encapsulated form, the active compound will normally be present in an amount of from about 2 to 98 percent by weight of the total composition.

In the preparation of dust, or wettable powder compositions, the toxicant products can be compounded with any of the finely divided solids, such as pyrophyllite, talc, chalk, gypsum, fuller's earth, bentonite, attapulgite, starch, cassein, gluten, or the like. In such operations, the finely divided carrier is ground or mixed with the toxicant or wet with a solution of the toxicant in a volatile organic solvent. Also, such compositions when employed as concentrates can be dispersed in water, with or without the aid of dispersing agents to form spray mixtures.

Granular formulations are usually prepared by impregnating a solution of the toxicant in a volatile organic solvent onto a bed of coarsely divided attapulgite, bentonite, diatomite, or the like.

Similarly, the toxicant products can be compounded with a suitable water-immiscible inert organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of inert water-immiscible solvent, emulsifying agent, and water. Preferred dispersing agents which can be employed in these compositions, are oil-soluble materials including non-ionic emulsifiers such as the condensation products of alkylene oxides with the inorganic acids, polyoxyethylene derivatives or sorbitan esters, complex ether alcohols, and the like. Also, oil-soluble ionic emulsifying agents such as mahogany soaps can be used. Suitable inert organic liquids which can be employed in the compositions include petroleum oils and distillates, toluene, liquid halohydrocarbons, and synthetic organic oils. The surface-active dispersing agents are usually employed in liquid compositions and in the amount of from 0.1 to 20 percent by weight of the combined weight of the dispersing agent and active compound.

In addition, other liquid compositions containing the desired amount of effective agent can be prepared by dissolving the toxicant in an inert organic liquid such as acetone, methylene chloride, chlorobenzene, or petroleum distillates. The preferred inert organic solvent carriers are those which are adapted to accomplish the penetration and impregnation of the plants and particularly soil with the toxicant compounds and are of such volatility as to leave little permanent residue thereon. Particularly desirable carriers are the petroleum distillates boiling almost entirely under 400° F. (204° C.) at atmospheric pressure and having a flash point above 80° C. The proportion of the compounds of this invention employed in a suitable solvent may vary from about 2 to about 50 percent or higher.

A preferred liquid composition includes the use of the active compound or compounds in combination with surface active dispersant agents only. In such compositions, it is preferred to use ionic and non-ionic blends of such dispersant agents in combination with one or more of the active materials. A particular advantage of such a formulation is that phytotoxicity associated with certain inert solvents, such as xylene, methylene chloride, or like materials can be avoided. Generally, the use of such formulations will result in compositions containing 75 percent or more of the active component.

Owing to the excellent suspensibility of the above formulation in water, it is convenient and often preferred to prepare and use aqueous concentrates as stock solutions themselves. In such practices, minor agitation results in a practical, stable formulation very adaptable for use in its concentrate form to treat soil in sprays or drenches. Additionally, if desired, the concentrates can be easily diluted with additional water for use as foliar spray treatments, soil drench treatments, and the like.

Water miscible organic solvents such as lower alcohols or propylene glycol can be added to depress the freezing point and further cooperate with the above system in that they are essentially non-phytotoxic.

The following examples further illustrate the present invention, but as such, are not to be construed as limiting in scope.

EXAMPLE XV

Test compounds of the invention were dissolved in acetone and the acetone solutions were diluted with water to provide dispersions containing various concentrations (parts per million by weight) of the compounds. The foliage of apple tree seedlings was sprayed to run off with the dispersions of test compounds. Four days after the treatment, the plants were inoculated with spores of *Venturia inaequalis*. One week after the inoculation, the percent control of apple scab disease was determined. The identity of test compounds, concentration thereof, and the results thereof are set forth in Table II.

TABLE II

| Compound of Example No. | Concentration of Test Compound, ppm | Percent Control of *Venturia inaequalis* at indicated concentration |
|---|---|---|
| II | 19 | 100 |
|  | 75 | 100 |
|  | 300 | 100 |
| IV | 19 | 75 |
|  | 75 | 93 |
|  | 300 | 100 |
| VII | 19 | 50 |
|  | 75 | 75 |
|  | 300 | 83 |
| IX | 19 | 83 |
|  | 75 | 100 |

TABLE II-continued

| Compound of Example No. | Concentration of Test Compound, ppm | Percent Control of *Venturia inaequalis* at indicated concentration |
|---|---|---|
| | 300 | 100 |

EXAMPLE XVI

Two series of tests were conducted by the procedure described in Example XV, except the plants were inoculated with spores of *Podosphaera leucotricha*. The results are set forth in Table III.

TABLE III

| Compound of Example No. | Concentration of Test Compound, ppm | Percent Control of *Podosphaera leucotricha* at indicated concentration | |
|---|---|---|---|
| | | First Series | Second Series |
| II | 19 | 50 | 90 |
| | 75 | 95 | 99 |
| | 300 | 100 | 100 |
| IV | 19 | 25 | 0 |
| | 75 | 95 | 50 |
| | 300 | 98 | 100 |
| V | 19 | 0 | 0 |
| | 75 | 0 | 0 |
| | 300 | 25 | 0 |
| VII | 19 | 0 | 25 |
| | 75 | 97 | 95 |
| | 300 | 100 | 100 |
| VIII | 19 | 0 | 0 |
| | 75 | 35 | 25 |
| | 300 | 98 | 90 |
| IX | 19 | 0 | 0 |
| | 75 | 0 | 0 |
| | 300 | 83 | 0 |
| X | 19 | 0 | 35 |
| | 75 | 0 | 95 |
| | 300 | 0 | 100 |

EXAMPLE XVII

This example demonstrates the systemic character of compounds of the invention. Aqueous compositions containing 0.4, 1.6, and 6.2 ppm of one of the test compound were prepared as described in Example XV. The compositions were drenched onto soil in which apple plant seedlings were growing. After one week, the plant foliage was sprayed with a suspension of spores of apple powdery mildew (*Podosphaera leucotricha*). When disease symptoms on control plants developed, evaluation of percent control on plants in treated pots was made. The results are set forth in Table IV.

TABLE IV

| Compound of Example No. | Percent Control of *Podosphaera leucotricha* at indicated concentration | | |
|---|---|---|---|
| | 0.4 ppm | 1.6 ppm | 6.3 ppm |
| II | 99 | 100 | 100 |
| IV | 93 | 100 | 100 |
| V | 0 | 25 | 50 |
| VI | 25 | 50 | 99 |
| VII | 99 | 99 | 98 |
| VIII | 50 | 90 | 99 |
| IX | 90 | 98 | 99 |
| X | 93 | 99 | 100 |
| XII | 0 | 0 | 25 |
| XIII | 0 | 0 | 35 |
| XIV | 0 | 35 | 97 |

What is claimed is:
1. A substituted 1-phenoxy-1-triazolyl-2-butanone compound corresponding to the formula

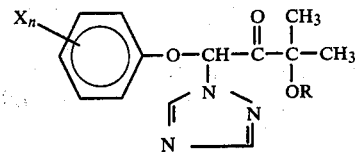

wherein each X independently represents chloro, bromo, iodo, nitro, methyl, methoxy, or methylthio; n represents an integer of 0 to 3; and R represents methyl or ethyl.

2. A compound as defined in claim 1 wherein X is chloro.

3. A compound as defined in claim 1 wherein R is methyl.

4. The compound as defined in claim 2 which is 1-(2,4-dichlorophenoxy)-1-(1H-1,2,4-triazol-1-yl)-3-methoxy-3-methyl-2-butanone.

5. The compound as defined in claim 2 which is 1-(2,4-dichlorophenoxy-1-(1H-1,2,4-triazol-1-yl)-3-ethoxy-3-methyl-2-butanone.

6. The compound as defined in claim 2 which is 1-(3,4-dichlorophenoxy)-1-(1H-1,2,4-triazol-1-yl)-3-methoxy-3-methyl-2-butanone.

7. The compound as defined in claim 2 which is 1-(4-chlorophenoxy)-1-(1H-1,2,4-triazol-1-yl)-3-methoxy-3-methyl-2-butanone.

8. The compound as defined in claim 1 which is 1-(4-iodophenoxy)-1-(1H-1,2,4-triazol-1-yl)-3-methoxy-3-methyl-2-butanone.

9. A fungicidal composition comprising as active ingredient a fungicidally effective amount of a substituted 1-phenoxy-1-triazolyl-2-butanone compound corresponding to the formula

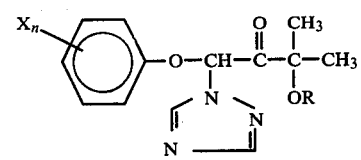

wherein each X independently represents chloro, bromo, iodo, nitro, methyl, methoxy, or methylthio; n represents an integer of 0 to 3; and R represents methyl or ethyl, in intimate admixture with an inert carrier therefor.

10. A composition as defined in claim 9 wherein X is chloro.

11. A composition as defined in claim 9 wherein R is methyl.

12. The composition as defined in claim 10 wherein the compound is 1-(2,4-dichlorophenoxy)-1-(1H-1,2,4-triazol-1-yl)-3-methoxy-3-methyl-2-butanone.

13. The composition as defined in claim 10 wherein the compound is 1-(2,4-dichlorophenoxy)-1-(1H-1,2,4-triazol-1-yl)-3-ethoxy-3-methyl-2-butanone.

14. The composition as defined in claim 10 wherein the compound is 1-(3,4-dichlorophenoxy)-1-(1H-1,2,4-triazol-1-yl)-3-methoxy-3-methyl-2-butanone.

15. The composition as defined in claim 10 wherein the compound is 1-(4-chlorophenoxy)-1-(1H-1,2,4-triazol-1-yl)-3-methoxy-3-methyl-2-butanone.

16. The composition as defined in claim 9 wherein the compound is 1-(4-iodophenoxy)-1-(1H-1,2,4-triazol-1-yl)-3-methoxy-3-methyl-2-butanone.

17. A method for controlling fungi that attack plants which comprises applying to plants, plant parts, or soil a composition containing as the active ingredient, a fungicidally effective amount of a substituted 1-phenoxy-1-triazolyl-2-butanone compound corresponding to the formula

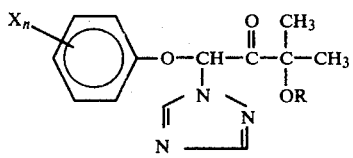

wherein each X independently represents chloro, bromo, iodo, nitro, methyl, methoxy, or methylthio; n represents an integer of 0 to 3; and R represents methyl or ethyl, in intimate admixture with an inert carrier therefor.

18. A method as defined in claim 17 wherein X is chloro.

19. A method as defined in claim 17 wherein R is methyl.

20. The method as defined in claim 18 wherein the active ingredient is 1-(2,4-dichlorophenoxy)-1-(1H-1,2,4-triazol-1-yl)-3-methoxy-3-methyl-2-butanone.

21. The method as defined in claim 18 wherein the active ingredient is 1-(2,4-dichlorophenoxy-1-(1H-1,2,4-triazol-1-yl)-3-ethoxy-3-methyl-2-butanone.

22. The method as defined in claim 18 wherein the active ingredient is 1-(3,4-dichlorophenoxy)-1-(1H-1,2,4-triazol-1-yl)-3-methoxy-3-methyl-2-butanone.

23. The method as defined in claim 18 wherein the active ingredient is 1-(4-chlorophenoxy)-1-(1H-1,2,4-triazol-1-yl)-3-methoxy-3-methyl-2-butanone.

24. The method as defined in claim 17 wherein the active ingredient is 1-(4-iodophenoxy)-1-(1H-1,2,4-triazol-1-yl)-3-methoxy-3-methyl-2-butanone.

* * * * *